Figure 1:
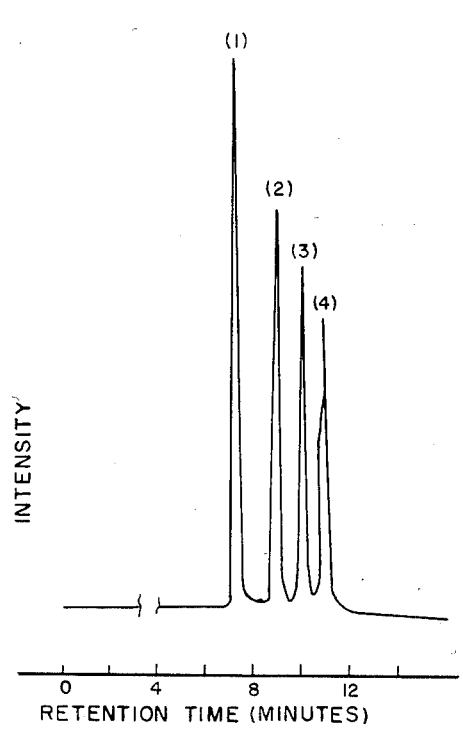

United States Patent [19]

Wada et al.

[11] Patent Number: 4,565,877

[45] Date of Patent: Jan. 21, 1986

[54] NAPHTHALENE DERIVATIVES AND METHOD FOR PREPARATION THEREOF

[75] Inventors: Hiroshi Wada, Omiya; Kazuhiro Ishii, Nara; Nobuchika Tsumagari, Habikino; Masaaki Matsuo, Kyoto; Mikio Matsumoto, Settsu, all of Japan

[73] Assignee: Tanabe Seiyaku Co., Ltd., Osaka, Japan

[21] Appl. No.: 540,414

[22] Filed: Oct. 11, 1983

[30] Foreign Application Priority Data

Oct. 21, 1982 [JP]  Japan ................................ 57-185884

[51] Int. Cl.$^4$ .................... C07C 53/42; C07D 205/04; C07D 207/48; C07D 211/96
[52] U.S. Cl. ................................ 548/530; 260/239 A; 260/544 B; 546/206; 210/656; 436/161; 436/174
[58] Field of Search ............ 260/544 B, 544 S, 239 A; 436/161, 174; 548/530; 546/206

[56] References Cited

U.S. PATENT DOCUMENTS 3,424,749  1/1969  Pfenninger .

OTHER PUBLICATIONS

Journal of the Pharmaceutical Science 68 (1979), No. 1 pp. 112–114.
Journal of Chromatography 152 (1978), pp. 413–419.
Berichte der Deutschen Chemischen Gesellschaft, Berlin, 35 (1902), 3779.

Primary Examiner—Natalie Trousof
Assistant Examiner—L. Hendriksen
Attorney, Agent, or Firm—Browdy and Neimark

[57] ABSTRACT

A naphthalene derivative of the formula:

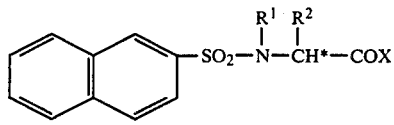

wherein $R^1$ is hydrogen and $R^2$ is lower alkyl or phenyl-lower alkyl; or $R^1$ and $R^2$ are combined together to form lower alkylene; X is halogen; and the absolute configuration at the asymmetric carbon atom shown by the asterisk is either (S)- or (R)-configuration, and a method of preparation thereof are disclosed. Said naphthalene derivative is useful as a chiral reagent for determining the optical purity of an optically active compound containing within its molecule at least one functional group selected from hydroxy, amino and imino groups.

6 Claims, 7 Drawing Figures

NAPHTHALENE DERIVATIVES AND METHOD FOR PREPARATION THEREOF

This invention relates to a novel optically active naphthalene derivative and a method for preparation thereof. It also relates to a method for determining the optical purity of an optically active compound by the use of said naphthalene derivative.

Said optically active naphthalene derivative of the present invention is represented by the following formula:

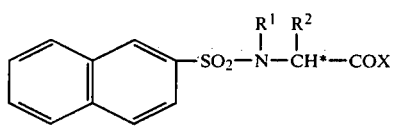

wherein $R^1$ is hydrogen and $R^2$ is lower alkyl or phenyl-lower alkyl; or $R^1$ and $R^2$ are combined together to form lower alkylene; X is halogen; and the absolute configuration at the asymmetric carbon atom shown by the asterisk is either (S)- or (R)-configuration.

Recently, a variety of optically active compounds have been used as drugs. Since optical isomers display different biochemical and pharmacological effects, however, the pharmacokinetic studies of each optical isomers of such drug are of great importance in evaluating the pharmacological effects thereof. In this connection, it is known that determination of the optical purity of such optically active drug or separation and quantitation of an optical impurity (i.e., an antipode) contained therein may be performed by either (i) liquid chromatography on columns prepared with asymmetric (optically active) staionary phase or using optically active mobile phases (hereinafter referred to as "direct method"); or (ii) reacting said drug with a chiral reagent to give a pair of diastereomers which can be resolved into each enantiomers by liquid chromatography (hereinafter referred to as "indirect method"). Among them, the direct method mentioned above is carried out by simple operations, but is still unsatisfactory in that chromatographic conditions can not be chosen ad libitum and is applicable to only a limited number of compounds.

On the other hand, chiral reagents which have been used in the above-mentioned indirect method include, for example, (d)-3-(2-naphthyl)propionyl chloride [Summary Report of Japanese Pharmaceutical Society's 101th Meeting, page 3C 11 - 5], (S)-(+)-2-octanol [Journal of the Pharmaceutical Sceience 68 (1979), No.1, pages 112–114], (−)-α-methoxy-α-methyl-1-naphthylacetic acid and (−)-α-methoxy-α-methyl-2-naphthylacetic acid [Journal of Chromatography 152 (1978), pages 413–419]. These indirect methods are applicable to a variety of optically active compounds by changing chromatographic conditions, offer higher sensitivity of detection and hence are much more efficient for determination of optical purity of samples. In determining the optical purity of each samples by the use of these chiral reagents, however the optical purity of said chiral reagents per se must be investigated prior to use because these reagents have been prepared by optical resolution of the corresponding racemic modifications and are not always available in optically pure form.

Generally, for the above-mentioned indirect method to be accurate (1) a chiral reagent to be used must be optically pure and (2) the reaction of said chiral reagent with an optically active compound must proceed quantitatively without racemization or epimerization. Moreover, (3) such chiral reagent must have a chromophore or fluorophore responding with a satisfactory sensitivity in a detector and at the same time (4) must have a functional group capable of forming a covalent linkage with said optically active compound.

As a result of various investigations, we have now found that the optically active naphthalene derivative [I] of the invention satisfies all the requirements (1) to (4) mentioned above and can be used advantageously as the chiral reagent for determination of the optical purity of an optically active compound containing within its molecule at least one functional group selected form the class consisting of hydroxy, amino and imino groups.

Representative examples of the optically active naphthalene derivative of the present invention include those of the formula [I] in which $R^1$ is hydrogen and $R^2$ is lower alkyl of one to five carbon atoms or phenyl-lower alkyl (said lower alkyl having one to three carbon atoms), or $R^1$ and $R^2$ are combined together to form alkylene of two to four carbon atoms, and X is halogen. Among them, a preferred subgenus is the derivative of the formula [I] in which $R^1$ is hydrogen and $R^2$ is lower alkyl of one to four carbon atoms (e.g., methyl, ethyl, n-propyl, isopropyl, n-butyl, isobutyl), benzyl or phenethyl, or $R^1$ and $R^2$ are combined together to form lower alkylene of two to four carbon atoms (e.g., ethylene, trimethylene, tetramethylene), and X is halogen (e.g., fluorine, bromine, chlorine). Further preferred subgenus is the derivative of the formula [I] in which $R^1$ is hydrogen and $R^2$ is methyl or benzyl, or $R^1$ and $R^2$ are combined together to form trimethylene. Preferred examples of the halogen atom (X) in the naphthalene derivative [I] are fluorine and chlorine atoms, among which chlorine atom is most suitable for use in the present invention.

According to the present invention, the optically active napthalene derivative [I] can be prepared by halogenating a compound of the formula:

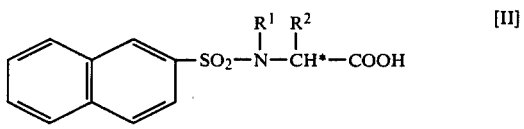

wherein $R^1$, $R^2$ and the asterisk are is defined above.

The halogenation of the compound [II] can be accomplished by treating it with a halogenating agent in a solvent. Preferred examples of the halogenating agent include oxalyl halide (e.g., oxalyl chloride), thionyl halide (e.g., thionyl chloride) and the like. Benzene, tetrahydrofuran and a mixture thereof are suitable as the solvent. It is preferred to carry out the reaction at a temperature between 10° and 80° C. This halogenation reaction proceeds advantageously without racemization of the starting compound [II], and the naphthalene derivative [I] of the invention in optically pure form can be readily obtained from the corresponding optically pure compound [II].

The compound [II] which is used as the starting material of the present invention is prepared, for example, by condensing an amino acid of the formula:

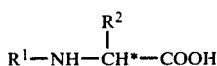

$$R^1-NH-CH^*-COOH \quad [III]$$

wherein $R^1$, $R^2$ and the asterisk are as defined above, with (2-naphthyl)sulfonyl chloride in accordance with the method described in Chemische Berichte Vol. 35, page 3783 (1902). Since this condensation also proceeds without racemization and the compound [III] used is a natural amino acid such as proline, alanine or phenylalanine, the starting compound [II] of the invention is easily obtained in optically pure form by the use of the optically pure amino acid [III] which is freely available in the market.

The naphthalene derivative [I] of the invention can be used for determining the optical purity of various optically active compounds which contain within the molecule thereof at least one functional group selected from the class consisting of hydroxy, amino and imino groups. Not only optically active compounds containing one asymmetric carbon atom within the molecule, but optically active compounds containing two or more asymmetric carbon atoms therein can also be used for this purpose. For example, hydroxy group-containing optically active compounds which are eligible for this purpose include optially active 3-hydroxy-cis and/or trans-2,3-dihydro-5-[2-(dimethylamino)ethyl]-2-(p-methoxyphenyl)-1,5-benzothiazepine-4(5H)-one, optically active 2-hydroxypentane, optically active 2-hydroxy-3-dimethyl-butane, optically active α-methylbenzylalcohol, optically active α-methyl-2-nitrobenzylalcohol, optically active 2-hydroxy-17-ethoxycarbonylheptadecane, optically active 2-hydroxy-phenylacetic acid, optically active 2-hydroxypropionic acid and so forth. Examples of amino group-containing optically active compounds which are eligible for the same purpose include optically active phenylglycine, optically active phenylalanine, optically active histidine, optically active cystein, optically active methionine, optically active leucine, optically active α-trifluoromethyl-benzylhydrazine, optically active α-methylbenzylamine, optically active α-methyl-2-chlorobenzylamine, optically active αmethyl-2-nitrobenzylamine, optically active α-methylphenethylamine, optically active α-methyl-2-chlorophenethylamine, optically active αmethyl-2-nitrophenethylamine, optically active 1-amino-1-(2-naphthyl)-ethane and so forth. Moreover, the naphthalene derivative [I] may be used for determination of optical purity of optically active compounds containing both of hydroxy and amino groups or both of hydroxy and imino groups within their molecules. Examples of such compounds are optically active p-hydroxyphenylglycine, optically active p-hydroxyphenylalanine, optically active 3,4-dihydroxyphenylalanin, optically active serine, optically active α-(3,4-dimethoxyphenethylaminomethyl)-4-hydroxybenzylalcohol, optically active α-(3,4-dimethoxyphenethylaminomethyl)-2-hydroxybenzylalcohol, optically active 5,7-dihydroxy-1-(3,4,5-trimethoxybenzyl)-1,2,3,4-tetrahydroisoquinoline, optically active 6,7-dihydroxy-1-(3,4,5-trimethoxybenzyl)-1,2,3,4-tetrahydroisoquinoline, optically active α-[(ethylamino)methyl]-m-hydroxybenzylalcohol, optically active m-hydroxy-α-(methylaminomethyl)benzylalcohol and so forth.

According to another embodiment of the present invention, optical purity of the optically active compound mentioned above can be determined by condensing it with the naphthalene derivative [I] to give the corresponding diastereomers, and subjecting said diastereomers to liquid chromatography.

The condensation of the optically active compound and the naphthalene derivative [I] can be conducted in the presence of an acid acceptor in a solvent. Examples of the acid acceptor include organic tertiary amines such as triethylamine, pyridine and the like. Methylene chloride, chloroform, ether, tetrahydrofuran and a mixture thereof are suitable as the solvent. It is preferred to carry out the reaction at a temperature between 5° C. and 30° C. In using for determining the optical purity of an optically active compound containing within its molecule at least one functional group selected from hydroxy, amino and imino groups, the absolute configuration of the naphthalene derivative [I] may be either (S)- or (R)- configuration irrespectively of the absolute configuration of said optically active compound.

The liquid chromatography of the diastereomers thus obtained is conducted in conventional manners such as those described in Japanese Pharmacopoeia 10th-Edition (English version), General Tests, pages 745–747. For example, it may be carried out by injecting said diastereomers into a chromatographic column (stationary phase) through an injection port using a microsyringe or sample valve, and then developing the column with a mobile phase solvent. This liquid chromatography may be carried out by means of partition chromatography, but it is generally preferred to carry it out by means of adsorption chromatography. It is especially preferrred to carry out the chromatography by means of high performance liquid chromatography irrespective of whether the adsorption chromatography or partition chromatography is empolyed for this purpose. Silica gel, alumina and the like are preferably used as the stationary phase for the adsorption chromatography. Alkyl-silica gel (e.g., octadecanyl-silica gel, nonyl-silica gel), aminoalkyl-silica gel (e.g., 3-aminopropyl-silica gel), cyanoalkyl-silica gel (e.g., 3-cyanopropyl-silica gel) and the like are suitable as the staionary phase for the partition chromatography. On the other hand, any solvents which are used as developing solvents for chromatography of the optically active compound to be tested can be used as the mobile phase solvent of the present invention. Such solvents include, for example, alkanes (e.g., n-pentane, n-hexane, n-heptane), halogenoalkanes (e.g., methylene chloride, chloroform, carbon tetrachloride, 1,2-dichloroethane), alkyl ether (e.g., methyl ether, ethyl ether, isopropyl ether, tetrahydrofuran, dioxane), cycloalkanes (e.g., cyclohexane), substituted or unsubstituted benzenes (e.g., benzene, toluene, nitrobenzene, phenol), alkanols (e.g., methanol, ethanol, propanol, butanol), alkyl alkanoate (e.g., methyl acetate, ethyl acetate), alkylamines (e.g., diethylamine, triethylamine), alkanoic amides or N-alkyl alkanoic amides (e.g., formamide, dimethylformamide), alkanones (e.g., acetone), alkanoic acids (e.g., acetic acid), alkanoyl nitriles (e.g., acetonitrile), dialkylsulfoxide (e.g, dimethylsulfoxide), water and a mixture of two or more solvents selected therefrom. In carrying out the liquid chromatography of the present invention, each diastereomers are separated preferably from each other by using one of these solvents or a mixture of two or more solvents (mixed in appropriate ratio) selected therefrom, depending on a particular optically active compound to be tested.

Each components of the diastereomers thus separated by the above-mentioned liquid chromatography can be readily detected by an ultraviolet absorbance detector and recorded on a recorder as a chromatogram. The quantity of each components recorded is estimated by measuring the peak area or peak height of the components on the chromatogram. Moreover, such quantity of each components can be measured by any one of "Internal Standard Method", "Area Percentage Method" or "Absolute Calibration Curve method" described in Japanese Pharmacopoeia 10th-Edition (English version), General Test, pages 738–740 and 745–747. Thus, the optical purity of the optically active compound used as a sample of the invention can be easily determined by comparing the quantitative ratio of said each components.

As mentioned hereinbefore, the naphthalene derivative [I] of the present invention is quite useful as a chiral reagent for determining the optical purity of a variety of optically active compounds (i.e., those containing within the molecule at least one functional group selected from hydroxy, amino and imino groups) by liquid chromatography, because it shows excellent reactivity toward said optically active compound and there is no racemization or epimerization during the derivaration reaction which converts said optically active compound into a diastereomeric mixture, and also because it has a chromophore responding with strong sensitivity in a UV detector. Another advantage of the naphthalene derivative [I] is that it always exists as solid at ambient temperature and is easy to handle in carrying out the experiments. Moreover, though the known chiral reagents have been prepared by optical resolution of the corresponding racemic modifications and are not always available in optically pure form, the naphthalene derivative [I] can be used for the purpose of the present invention without investigating the optical purity thereof prior to use because said naphthalene derivative [I] can be always prepared in optically pure form, i.e., without racemization, from the corresponding optically pure amino acid available in the market. Further, as compared with the known chiral reagents such as (d)-3-(2-naphthyl)propionyl chloride, the naphthalene derivative [I] of the invention shows higher separation efficiency of each diasteromers and is much more effective for determining the optical purity of an optically active compound. For example, when the optical purity of dl-3-hydroxy-cis/trans-2,3-dihydro-5-[2-dimethylamino)ethyl]-2-(p-methoxyphenyl)-1,5-benzothiazepine-4(5H)-one (referred to below as "sample") is examined by reacting it with (S)-1-(2-naphthylsulfonyl)-pyrrolidin-2-carbonyl chloride (a chiral reagent) of the invention and then subjecting the resultant diastereomers to liquid chromatography, each four isomers (i.e., d-cis, l-cis, d-trans and l-trans isomers) of said sample are separated completely on the chromatogram and the quantitaive ratio of these four isomers are easily estimated therefrom, though (d)-3-(2-naphthyl)propionyl chloride when used as a chiral reagent instead of the naphthalene derivative shows [I] incomplete separation of each isomers of said sample and makes it possible to separate it into only the dl-trans and dl-cis isomers thereof on the chromatogram.

Practical and presently-preferred embodiments of the present invention are illustratively shown in the following Examples.

EXAMPLE 1

15.6 g of (S)-1-(2-naphthylsulfonyl)pyrrolidine-2-carboxylic acid [Chem, Ber., 35, 3783 (1902)] are dissolved in 120 ml of anhydrous benzene, and 17.5 ml of oxalyl dichloride are added dropwise thereto under stirring. The mixture is allowed to stand at 40° to 50° C. overnight. Then, the mixture is condensed to dryness under reduced pressure, and the residue is recrystallized from a mixture of n-hexane and benzene. 14.3 g of (S)-1-(2-naphthylsulfonyl)pyrrolidine-2-carbonyl chloride are obtained.

M.p. 107°–109° C.
IR$\nu_{max}^{Nujol}$ (cm$^{-1}$): 1780, 1340, 1205, 1150
Mass m/e: 325, 323 (M+)
$[\alpha]_D^{20}$ −81.6° (C=1, chloroform)

EXAMPLE 2

2 g of (S)-2-(2-naphthylsulfonylamino)propionic acid are added to 50 ml of anhydrous benzene, and 2.04 ml of thionyl chloride are added thereto. The mixture is stirred at 40° to 50° C for 18 hours. The reaction mixture is condensed to dryness under reduced pressure, and the residue is recrystallized from a mixture of benzene and n-hexane. 1.6 g of (S)-2-(2-naphthylsulfonylamino)propionyl chloride are obtained.

M.p. 134.5°–136.5° C.
IR$\nu_{max}^{Nujol}$ (cm$^{-1}$): 3280, 1820, 1800, 1765, 1150
Mass m/e: 299, 297 (M+)
$[\alpha]_D^{20}$ −6.2° (C=1, chloroform)

EXAMPLE 3

4 g of (S)-2-(2-naphthylsulonylamino)-3-phenyl-propionic acid are dissolved in 40 ml of anhydrous benzene-anhydrous tetrahydrofuran (3:1), and 3.2 ml of thionyl chloride are added thereto. The mixture is stirred at 40° to 50° C for 18 hours. The reaction mixture is condensed to dryness under reduced pressure, and the residue is recrystallized from a mixture of benzene and n-hexane. 3.2 g of (S)-2-(2-naphthylsulfonylamino)-3-phenyl-propionyl chloride are obtained.

M.p. 141°–143° C.
IR$\nu_{max}^{Nujol}$ (cm$^{-1}$): 3260, 1800, 1780, 1340, 1150
Mass m/e : 375, 373 (M+)
$[\alpha]_D^{20}$ −4.7° (C=1, chloroform)

EXAMPLE 4

1 (1) (Preparation of a sample)

10 mg of a mixture consisting of an approximately equimolar amount of dl-3-acetoxy-cis-2,3-dihydro-5-[2-(dimethylamino)ethyl]-2-(p-methoxyphenyl)-1,5-benzothiazepine-4(5H)-one hydrochloride (Japanese patent publication (examined) No. 813/1972) and dl-3-acetoxy-trans-2,3-dihydro-5-[2-(dimethylamino)ethyl]-2-(p-methoxyphenyl)-1,5-benzothiazepine-4(5H)-one hydrochloride (Chem. Pharm. Bull, 19 (1971), 595) are dissolved in 30 ml of methanol, and 5 ml of a 0.1 N sodium hydroxide solution are added thereto. The mixture is diluted with methanol to a total volume of 50 ml. Then, the mixture is allowed to stand at room temperature for one hour. 20 ml of the mixture are collected therefrom and evaporated to remove methanol. 20 ml of water and 10 ml of chloroform are added to the residue obtained. After shaking, 3 ml of the chloroform layer are taken therefrom and evaporated to remove chloroform. dl-3-hydroxy-cis/trans-2,3-dihydro-5-[2-(dimethylamino)ethyl]-2-(p-methoxyphenyl)-1,5-benzothiazepine-4(5H)-one is thereby obtained as a sample.

(2) (Preparation of diasteromers)

20 mg of (S)-1-(2-naphthylsulfonyl)pyrrolidine-2-carbonyl chloride, 0.5 ml of methylene chloride and 20 μl of pyridine are added to the sample obtained in paragraph (1). The mixture is allowed to stand at room temperature for 15 minutes. Then, the mixture is diluted with chloroform to a total volume of 20 ml. A solution of four diastereomers, i.e., dl-3-[(S)-1-(2-naphthylsulfonyl)pyrrolidine-2-carbonyloxy]-cis/trans-2,3-dihydro-5-[2-(dimethylamino)-ethyl]-2-(p-methoxyphenyl)-1,5-benzothiazepine-4(5H)-one, is thereby obtained.

(3) (Determination of optical purity)

20 ml of the solution of four diastereomers obtained in paragraph (2) is applied to high performance liquid chromatography under the conditions mentioned below. The chromatogram obtained is shown in FIG. 1. This chromatogram indicates that the optical purity of d-3-hydroxy-cis-2,3-dihydro-5-[2-(dimethylamino)ethyl]-2-(p-methoxyphenyl)-1,5-benzothiazepine-4(5H)-one in the sample is 26.7 w/w %. This chromatogram also indicates that the sample contains 25.1 w/w % of l-3-hydroxy-cis-2,3-dihydro-5-[2-(dimethylamino)-ethyl]-2-(p-methoxyphenyl)-1,5-benzothiazepine-4(5H)-one and 24.6 to 23.5 w/w % of each one of d-3-hydroxy-trans-2,3-dihydro-5-[2-(dimethylamino)ethyl]-2-(p-methoxyphenyl)-1,5-benzothiazepine-4(5H)-one and l-3-hydroxy-trans-2,3-dihydro-5-[2-(dimethylamino)ethyl]-2-(p-methoxyphenyl)-1,5-benzothiazepine-4(5H)-one, respectively.

[Conditions]

Column: Silica gel (15 cm×4.6 mm in i.d.)
Mobile phase: Chloroform - methylene chloride - methanol - diethylamine (800:200:12:0.4)
Temperature of column: 40° C.
Detector: UV 254 nm [Shimadzu UV-2 absorbance detector (Shimadzu Corporation, Kyoto, Japan)]
Flow speed: one ml/minute
Attenuation: 0.32 AUFS (Absorbance unit full scale)
Concomitantly, the numerals (1) to (4) in FIG. 1 stand for the absorbance peaks of compounds derived from the following samples.

(1): d-3-hydroxy-cis-2,3-dihydro-5-[2-(dimethylamino)-ethyl]-2-(p-methoxyphenyl)-1,5-benzothiazepine-4(5H)-one
(2): l-3-hydroxy-cis-2,3-dihydro-5-[2-(dimethylamino)-ethyl]-2-(p-methoxyphenyl)-1,5-benzothiazepine- 4(5H)-one
(3) & (4): d-3-hydroxy-trans-2,3-dihydro-5-[2-(dimethyl-amino)ethyl]2-(p-methoxyphenyl)-1,5 benzothiazepine-4(5H)-one and l-3-hydroxy-trans-2,3-dihydro-5-[2-(dimethylamino)ethyl]-2-(p-methoxyphenyl)-1,5-benzothiazepine-4(5H)-one

EXAMPLE 5

(1) (Preparation of a sample and diastereomers)

10 mg of d-3-acetoxy-cis-2,3-dihyro-5-[2-(dimethylamino)ethyl]-2-(p-methoxyphenyl)-1,5-benzothiazepine-4(5H)-one hydrochloride prepared according to the method described in Japanese patent publication (examined) No. 18038/1978 is treated in the same manner as described in Example 4-(1). d-3-hydroxy-cis-2,3-dihydro-5-[2-(dimethylamino)ethyl]-2-(p-methoxyphenyl)-1,5-benzothiazepine-4(5H)-one thus obtained is further treated in the same manner as described in Example 4-(2), whereby the corresponding diastereomer is obtained.

(2) (Determination of optical purity)

Figure 2:
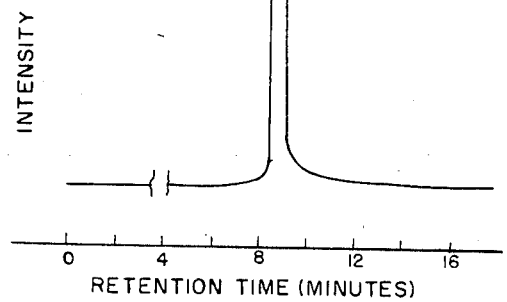

The diastereomer obtained in paragraph (1) is applied to high performance liquid chromatography under the same conditions as described in Example 4-(3). The chromatogram obtained is shown in FIG. 2. This chromatogram indicates that d-3-hydroxy-cis-2,3-dihydro-5-[2-(dimethylamino)ethyl]-2-(p-methoxyphenyl)-1,5-benzothiazepine-4(5H)-one used as the sample in paragraph (1) is optically pure and quite free from its levorotatory enantiomer.

EXAMPLE 6

(1) (Preparation of a sample and diastereomers)

To optically pure d-3-acetoxy-cis-2,3-dihydro-5-[2-(dimethylamino)ethyl]-2-(p-methoxyphenyl)-1,5-benzothiazepine -4(5H)-one hydrochloride are added 0.5 w/w % of its corresponding l-cis isomer hydrochloride and one w/w % of its correpsonding dl-trans isomer hydrochloride. The mixture thus obtained is treated in the same manner as described in Example 4-(1) & (2), whereby the corresponding diastereomers are obtained.

(2) (Determination of optical purity)

Figure 3:
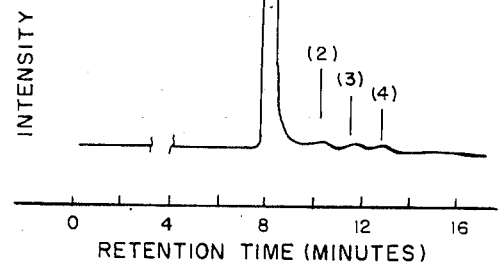

The diastereomers obtained in paragraph (1) is applied to high performance liquid chromatography under the same conditions as described in Example 4-(3). The chromatogram obtained is shown in FIG. 3. This chromatogram indicates that even 0.5 w/w % of the optical impurities contained in the above-mentioned d-cis enantiomer can be detected by the use of (S)-1-(2-naphthylsulfonyl)pyrrolidine-2-carbonyl chloride.

EXAMPLE 7

(1) (Preparation of diastereomers)

10 mg of dl-α-(3,4-dimethoxyphenethylaminomethyl)-4-hydroxybenzylalcohol prepared according to the method described in Japanese patent publication (examined) No. 10974/1978 are dissolved in 100 μl of glacial acetic acid, and the solution is diluted with methylene chloride to a total volume of 30 ml. 3 ml of the solution are collected therefrom, and 30 μl of triethylamine and 10 mg of (S)-1-(2-naphthylsulfonyl)pyrrolidine-2-carbonyl chloride are added thereto. The mixture is allowed to stand at room temperature for 15–20 minutes. Then, 100 μl of triethylamine are added to the mixture, and said mixture is further diluted with methylene chloride to a total volume of 10 ml. A solution of diastereomers, i.e., dl-α-{N-[(S)-1-(2-naphthylsulfonyl)-pyrrolidine-2-carbonyl]-3,4-dimethoxyphenethylaminomethyl}-4-[(S)-1-(2-naphthylsulfonyl)pyrrolidine-2-carbonyloxy]benzylalcohol, is thereby obtained.

(2) (Determination of optical purity)

Figure 4:
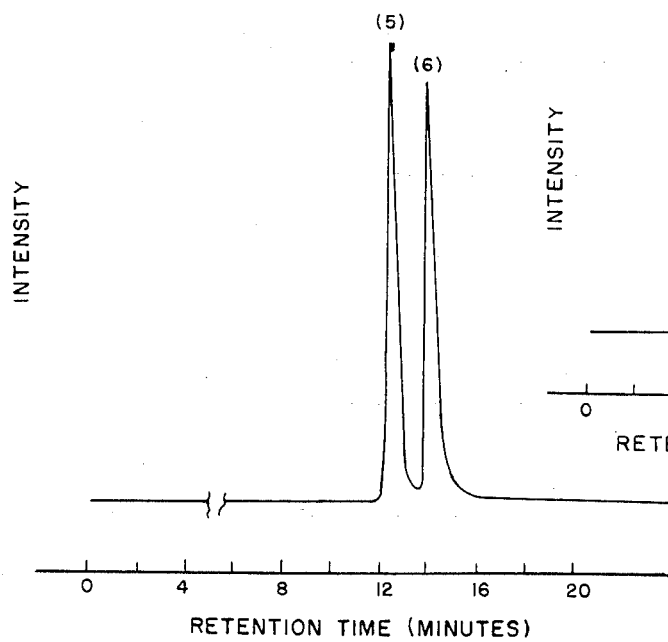

20 μl of the solution of diastereomers obtained in paragraph (1) is applied to high performance liquid chromatography under conditions mentioned below. The chromatogram obtained is shown in FIG. 4. This chromatogram indicates that the optical purity of l-α-(3,4-dimethyoxyphenethylaminomethyl)-4-hydroxybenzylalcohol in the sample is 50 w/w %. This chromatogram also indicates that the sample contains 50 w/w % of d-α-(3,4-dimethoxyphenethylaminomethyl)-4-hydroxybenzylalcohol.

[Conditions]

Column: Silica gel (15 cm×4.6 mm in i.d.)
Mobile phase: Methylene chloride - methyl acetate (80:1)
Temperature of column: 40° C.
Detector: UV 254 nm [Shimadzu UV-2 absorbance detector]
Flow speed: one ml/minute
Attenuation: 0.32 AUFS Concomitantly, the numerals (5) to (6) in FIG. 4 stand for the absorbance peaks of compounds derived from the following samples.

(5): d-α-(3,4-dimethoxyphenethylaminomethyl)-4-hydroxybenzylalcohol
(6): l-α-(3,4-dimethyoxyphenethylaminomethyl)-4-hydroxybenzylalcohol

EXAMPLE 8

(1) (Preparation of diastereomers)

10 mg of l-α-(3,4-dimethoxyphenethylaminomethyl)-4-hydroxybenzylalcohol prepared according to the method described in Japanese patent publication (examined) No. 16501/1980 are treated in the same manner as described in Example 7-(1), whereby the corresponding diastereomer is obtained.

(2) (Determination of optical purity)

Figure 5:
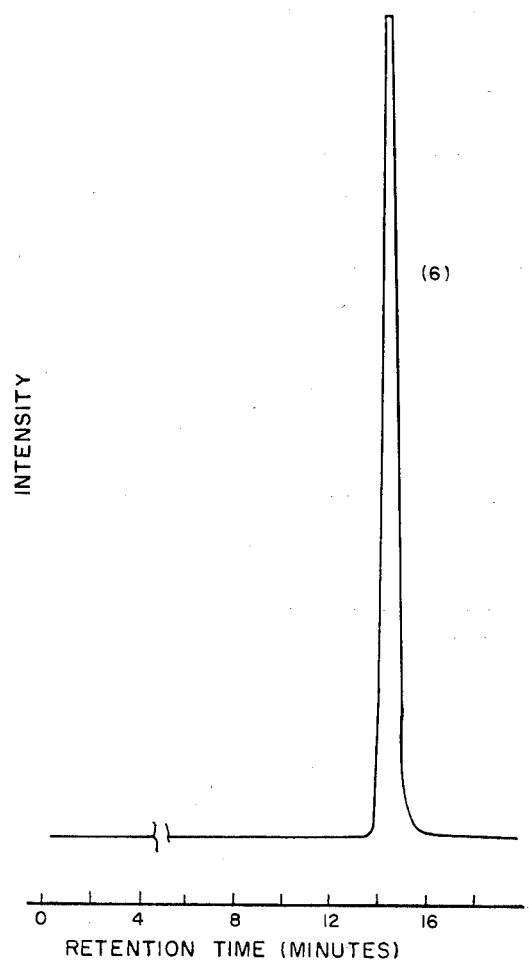

The diastereomer obtained in paragraph (1) is applied to high performance liquid chromatography under the safe conditions as described in Example 7-(2). The chromatogram obtained is shown in FIG. 5. This chromatogram indicates that l-α-(3,4-dimethoxyphenethylaminomethyl)-4-hydroxybenzylalcohol used as the sample in paragraph (1) is optically pure.

EXAMPLE 9

(1) (Preparation of diastereomers)

To optically pure l-α-(3,4-dimethoxyphenethylaminomethyl)- 4-hydroxybenzylalcohol is added one w/w % of its corresponding d-isomer, and the mixture is treated in the same manner as described in Example 7-(1), whereby the corresponding diastereomers are obtained.

(2) (Determination of optical purity)

Figure 6:
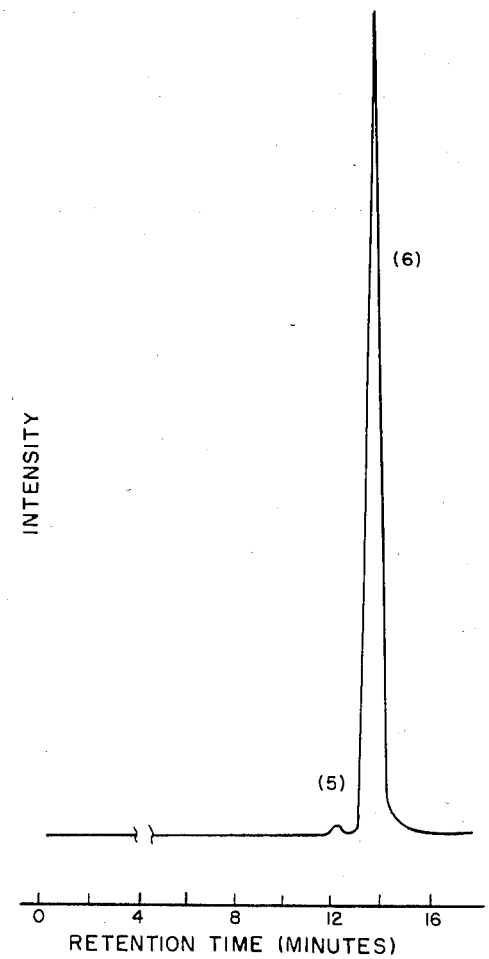

The diastereomers obtained in paragraph (1) is applied to high performance liquid chromatography under the same conditions as described in Example 7-(2). The chromatogram obtained is shown in FIG. 6. This chromatogram indicates that even one w/w % of the optical impurity (d-isomer) contained in the above-mentioned l-enantiomer can be detected by the use of (S)-1-(2-naphthylsulfonyl)pyrrolidine-2-carbonyl chloride.

EXAMPLE 10

(1) (Preparation of diastereomers)

10 mg of dl-5,7-dihydroxy-1-(3,4,5-trimethoxybenzyl)-1,2,3,4-tetrahydroisoquinoline prepared according to the method described in Japanese patent publication (examined) No. 47474/1977 are dissolved in 30 ml of methylene chloride. 3 ml of the solution are collected therefrom, and 30 μl of triethylamine and 10 mg of (S)-1-(2-naphthylsulfonyl)pyrrolidine-2-carbonyl chloride are added to the collected solution. The mixture is allowed to stand at room temperature for 15–20 minutes. Then, the mixture is diluted with methylene chloride to a total volume of 10 ml. A solution of diastereomers, i.e., 5,7-di-[(S)-1-(2-naphthylsulfonyl)pyrrolidine-2-carbonyloxy] -1-(3,4,5-trimethoxybenzyl)-1,2,3,4-tetrahydroisoquinoline, is obtained.

(2) (Determination of optical purity)

Figure 7:
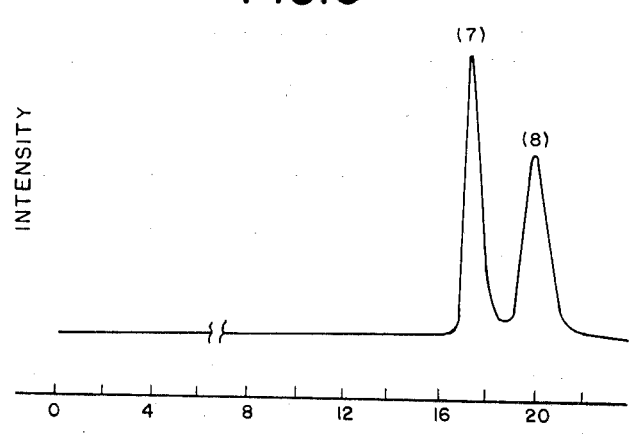

20 μl of the solution of diastereomers obtained in paragraph (1) is applied to high performance liquid chromatography under conditions mentioned below. The chromatogram obtained is shown in FIG. 7. This chromatogram indicates that the optical purity of l-5,7-dihydroxy-1-(3,4,5-trimethoxybenzyl)-1,2,3,4-tetrahydroisoquinoline in the sample is 50 w/w %. This chromatogram also indicates that the sample contains 50 w/w % of d-5,7-dihydroxy-1-(3,4,5-trimethoxybenzyl)-1,2,3,4-tetrahydroisoquinoline.

[Conditions]

Column: Silica gel (15 cm×4.6 mm in i.d.)
Mobile phase: Methylene chloride - methyl acetate (80:3)
Temperature of column: 40° C.
Detector: UV 254 nm [Shimadzu UV-2 absorbance detector]
Flow speed: one ml/minute
Attenuation: 0.32 AUFS Concomitantly, the numerals (7) to (8) in FIG. 7 stand for the absorbance peaks of compounds derived from the following samples.

(7): d-5,7-dihydroxy-1-(3,4,5-trimethoxybenzyl)-1,2,3,4-tetrahydroisoquinoline
(8): l-5,7-dihydroxy-1-(3,4,5-trimethoxybenzyl)-1,2,3,4-tetrahydroisoquinoline

What we claim is:

1. An optically active naphthalene derivative of the formula:

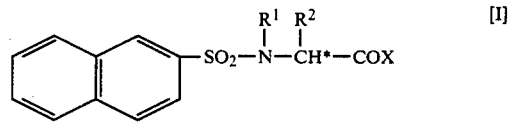

wherein $R^1$ is hydrogen and $R^2$ is lower alkyl or phenyl-lower alkyl; or $R^1$ and $R^2$ are combined together to form alkylene of 2–4 carbons; X is halogen; and the absolute configuration at the asymmetric carbon atom shown by the asterisk is either (S)- or (R)-configuration.

2. The naphthalene derivative claimed in claim 1, in which $R^1$ is hydrogen and $R^2$ is alkyl of one to 4 carbon atoms, benzyl or phenethyl; or $R^1$ and $R^2$ are combined together to form alkylene of 2 to 4 carbon atoms.

3. The naphthalene derivative claimed in claim 1, in which $R^1$ is hydrogen and $R^2$ is methyl or benzyl; or $R^1$ and $R^2$ are combined together to form trimethylene.

4. The naphthalene derivative claimed in claim 2 in which X is chlorine or fluorine atom.

5. The naphtalene derivative claimed in claim 3, in which X is chlorine or fluorine atom.

6. An optically active naphthalene derivative of the formula:

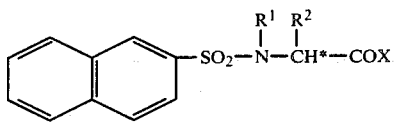
wherein $R^1$ is hydrogen and $R^2$ is alkyl of one to 5 carbon atoms or phenyl-lower alkyl, said alkyl having one to three carbon atoms; X is halogen; or $R^1$ and $R^2$ are combined to form alkylene of 2–4 carbon atoms; X is halogen; and the absolute configuration at the asymmetric carbon atom shown by the asterisk is either (S)- or (R)-configuration.
* * * * *